United States Patent [19]
Karami et al.

[11] Patent Number: 5,193,225
[45] Date of Patent: Mar. 16, 1993

[54] ELASTIC BAND

[75] Inventors: Hamzeh Karami, Mansfield; Ronald F. Vitaris, Worcester, both of Mass.

[73] Assignee: Manufacturers Hanover Trust Company

[21] Appl. No.: 580,221

[22] Filed: Sep. 10, 1990

[51] Int. Cl.⁵ .............................................. A41F 9/00
[52] U.S. Cl. .......................................... 2/312; 2/311; 2/314; 2/315; 2/338; 2/220; 2/221
[58] Field of Search .................. 2/312, 311, 313, 314, 2/315, 171.8, 209.1, DIG. 11, 236, 220, 221, 338; 66/172 E; 428/230

[56] References Cited

U.S. PATENT DOCUMENTS

| | | | |
|---|---|---|---|
| 1,884,310 | 10/1932 | Sime | 2/314 |
| 2,211,137 | 8/1940 | Lesselbaum | 2/315 |
| 2,235,690 | 3/1941 | Teague et al. | 428/230 |
| 2,401,132 | 5/1946 | Boecker | 2/338 |
| 2,425,397 | 8/1947 | Roseman | 2/315 |
| 3,078,469 | 2/1963 | Lynam | 2/338 |
| 3,094,990 | 6/1963 | Neilson | 2/400 |
| 3,359,571 | 12/1967 | Burke | 2/312 |
| 3,590,390 | 7/1971 | Howard et al. | 2/312 |
| 4,413,623 | 11/1983 | Pieniak | 428/230 |
| 4,582,550 | 4/1986 | Sigl | 428/230 |
| 4,932,079 | 6/1990 | Bridgewater | 2/313 |

FOREIGN PATENT DOCUMENTS 256743 1/1967 Austria ................................. 2/221

Primary Examiner—Werner H. Schroeder
Assistant Examiner—Gloria Hale

[57] ABSTRACT

An elastic band comprising a plurality of spaced elastic members and a pair of flexible sheet materials on opposed sides of the elastic members, the elastic members being secured in a stretched position to each of said flexible sheet materials.

7 Claims, 1 Drawing Sheet

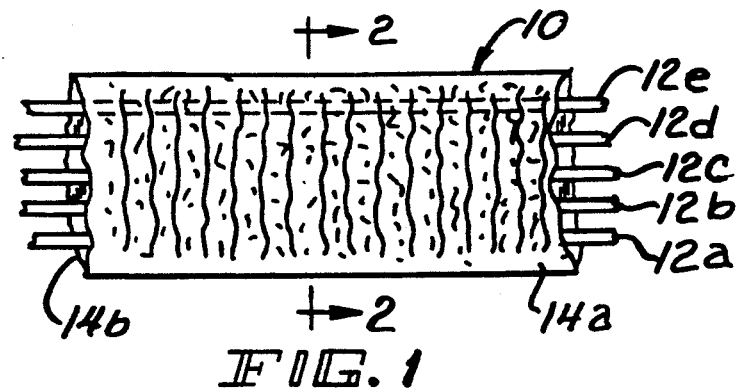
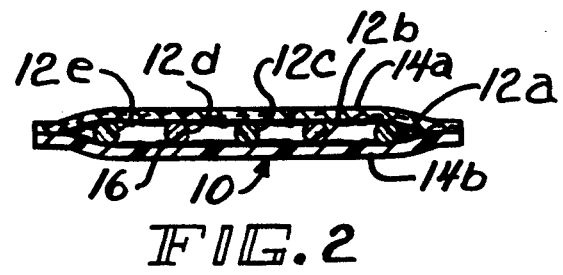
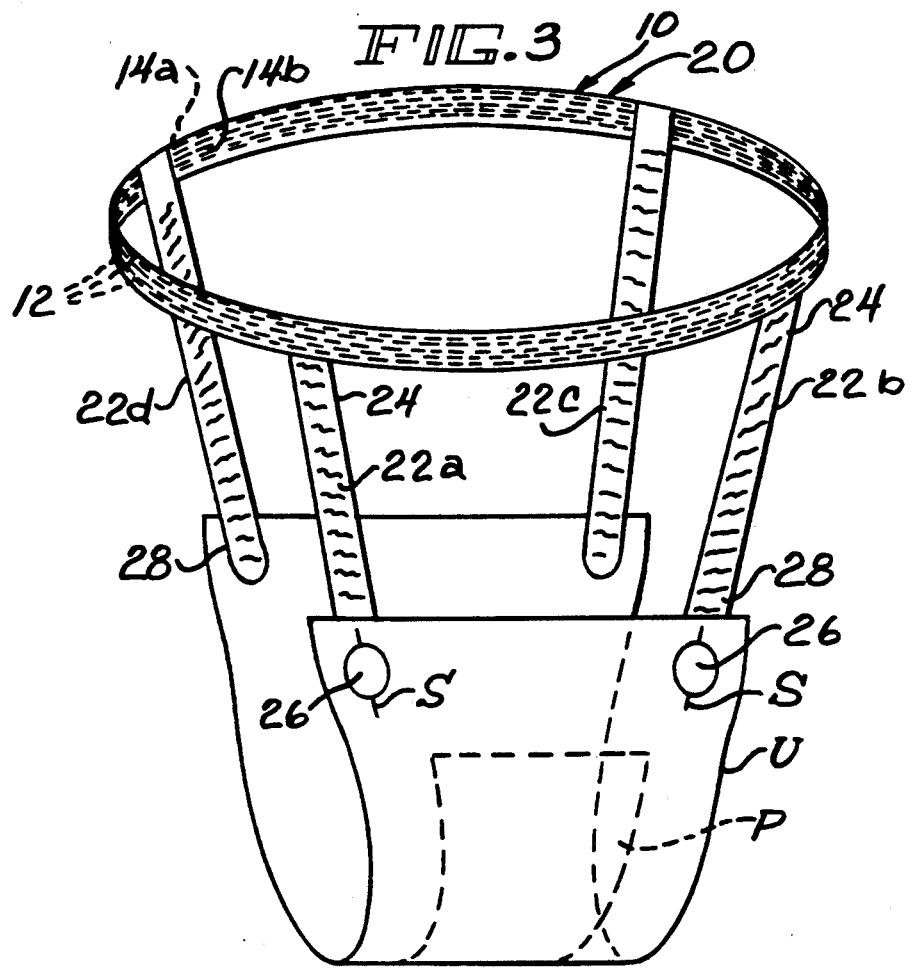

ELASTIC BAND

RELATED APPLICATION

This application is related to Applicant's copending application Ser. No. 580,421, filed concurrently.

BACKGROUND OF THE INVENTION

The present invention relates to novel elastic bands or strips.

Before the present invention, elastic members, such as elastic bands have been known for various uses including, but not limited to disposable undergarments such as diapers, underpads, sanitary napkins and the like, belts for medical and/or personal hygiene uses, articles of clothing such as belts and suspenders, medical and surgical products such as support bandages, elastic bandage rolls, etc. In general, such elastic bands may comprise a single elongated elastic strip having a desired width, or fabric having suitable elastic in the fabric, such as for a waistband, However, the single width of elastic bands may not provide the desired degree of comfort when an article containing the band is worn. In addition, it is desired to simplify the construction and reduce the cost of elastic members so that they may be disposable.

Stated simply, the task of the present invention, accordingly, is to provide in a more cost-efficient manner, elastic bands having improved comfort when worn in articles such as those described above.

SUMMARY OF THE INVENTION

In accordance with the present invention, this task is solved in a simple and elegant manner by providing elastic bands comprising a plurality of spaced elastic members and a pair of flexible sheets on opposed sides of the elastic members sandwiching the elastic members therebetween, the elastic members being secured to the flexible sheets when stretched from their relaxed condition.

A feature of the invention is that the elastic members gather the sheets after the sheets are secured to the elastic members and the elastic members are relaxed.

Another feature of the invention is that the elastic members distribute the forces when applied against a wearer in order to provide additional comfort to the wearer during use.

Still another feature of the invention is the provision of a support for a disposable undergarment such as a diaper or sanitary napkin utilizing the novel elastic bands of the present invention.

Other objects and features of the invention will be obvious in the light of the following detailed description taken in conjunction with the accompanying drawing and the appended claims.

BRIEF DESCRIPTION OF THE DRAWING

FIG. 1 is a fragmentary plan view of an elastic band of the present invention;

FIG. 2 is a sectional view taken substantially as indicated along the line 2—2 of FIG. 1; and FIG. 3 is a perspective view of an elastic undergarment support of the present invention.

DETAILED DESCRIPTION OF THE INVENTION

Referring now to FIG. 1, there is shown an elastic band generally designated 10 having a plurality of elongated spaced elastic members or strands 12a, 12b, 12c, 12d and 12e. While they preferably have a circular cross section, as shown in FIG. 2, it will be appreciated that they may if desired be of other configuration. With reference to FIGS. 1 and 2, the band 10 has a pair of opposed flexible sheet materials 14a and 14b which are secured to opposed sides of the elastic members 12a, b, c, d and e by suitable means, such as adhesive 16 or by heat sealing.

The elastic members 12a, b, c, d and e may be made from a suitable per se known elastomeric material such as natural, butyl or synthetic rubber, polyurethane, elastic yarns and the like.

Flexible sheets 14a and 14b, which may be the same or different, may comprise a woven or nonwoven fabric or a plastic material such as a polyolefin, e.g. polyethylene, polypropylene, or polyisobutylene, a polyester such as polyethylene terephthalate, a cellulose ester such as cellulose acetate or triacetate, etc.

Adhesive 16 may comprise any of the per se known hot melt or other adhesives, e.g. acrylic or rubber-based, which are sufficiently aggressive to retain their adhesiveness under stress to the respective sheet and elastic member substrates. Since such adhesives are well known, their selection will be a matter of individual choice within the expected judgment of the skilled worker in the light of the instant description.

While the particular method for preparing bands 10 is not critical to the practice of this invention, they may for example be made in the following manner.

The elastic members are first stretched under tension to the desired length, e.g. on the order of 2-3 times their length in the relaxed condition. A hot melt or other adhesive may then be applied, e.g. by spraying, on the elastic members while they are maintained in the stretched condition and in spaced relationship, as shown in FIG. 2. Proper bonding of the elastic members to sheets 14a and 14b may then be accomplished by passing an assembly comprising the adhesive-coated elastic member sandwiched between sheets 14a and 14b through the nip of two superposed pressure-applying rollers maintained at a gap and at a temperature, e.g. an elevated temperature, sufficient to perfect bonding.

Following securement of the elastic members to the outer sheets to form a large elongated band 10 which may, for example, be on the order of 12-36 inches in width and 50-300 feet in length, the resulting band may be taken up on a suitable roll for shipment or storage. Alternatively, it may be subjected to a slitting and severing operation where the band is passed through a series of slitting knives to provide a plurality of bands of the desired width, after which the bands are severed to the desired length. The resulting bands then may be taken up on rolls for shipment to their destination for further use or they then be transported to another station at the manufacturing facility for immediate use, e.g. in the manufacture of the elastic crotch portion in the assembly of disposable diapers. As will be appreciated, the aforementioned method for preparing the bands may alternatively be incorporated into a continuous manufacturing process for preparing an undergarment or other desired article containing the band.

An important advantage of the elastic bands 10 of the present invention is that they distribute forces laterally along the width of the band when applied to a wearer to provide improved comfort to the wearer during use.

Another significant advantage is that their construction is simplified and highly cost-efficient, thus providing a commercially feasible method of making elastic bands which may be disposable after use.

A support generally designated 20 according to this invention for an undergarment U having a pad P is illustrated in FIG. 3, in which like reference numerals designate like parts. In this form, the support 20 has an elastic band generally designated 10 which is constructed in the manner as disclosed in connection with the description of the band of FIGS. 1 and 2 and which for purposes of illustration is shown to be endless. Thus, the band has a plurality of elongated elastic members 12 sandwiched in spaced relationship between opposed flexible sheets 14a and 14b with the elastic members being secured in stretched condition to the sheets, as described. Support 20 has a plurality of elastic securement strips 22a, 22b, 22c and 22d which are preferably elastic, e.g. constructed in the manner as previously described with elastic band 10 of FIGS. 1 and 2.

The strips 22a, b, c and d have one end 24 secured at spaced locations to the elastic band 10, and have securement devices 26 secured to the opposed ends 28 of the strips. These securement devices 26 may comprise suitable buttons which can be received in slits or button holes S in opposed ends of the undergarment U.

In use, the support 20 may be placed on the wearer with the elastic band 10 positioned about the waist, after which the band 20 is relaxed in order to assume a snug position on the wearer's waist to retain the undergarment in place, with the securement strips 22a, b, c and d depending from the elastic band 10. The securement devices 26 are then attached to the undergarment to secure it in place on the wearer. Where the securement devices are buttons, they are received in slits S for securement.

As will be apparent, the undergarment U may be replaced by another without removal of support 20 from the wearer, simply by disengaging the undergarment from the securement strips and then attaching another in like manner. Alternatively, of course, the support 20 may be removed and discarded after a single use.

It will be appreciated that various changes may be made without departing from the scope of the invention herein contemplated.

For example, while support 20 is shown, for purposes of illustration, as having an endless elastic band 10, it will be appreciated that the band need not be endless but may instead be provided with suitable closure means, e.g. snaps, hooks and the like to releasably secure the ends together. While the securement strips 22 are preferably elastic, inelastic strips are also contemplated. The strips may be permanently secured at end 24 to band 10 or they may be provided with means for releasably engaging band 10. For example, ends 24 may form loops, similar to belt loops, through which band 10 may be threaded. Other fastening means will be readily suggested to those skilled in the art.

Since certain changes may be made without departing from the scope of the invention herein contemplated, it is intended that all matter contained in the foregoing description and drawing shall be taken as illustrative and not in a limiting sense.

What is claimed is:

1. A support for an undergarment comprising:
   an elastic belt having a plurality of elongated spaced elastic members in a stretched conditions; said elastic members also having opposed sides and being sandwiched between a pair of flexible strips while in the stretched condition; and
   a plurality of securement strips having two ends, wherein one end is secured to the belt and the other end of each respective securement strip having means for releasably securing the strips to the undergarment, the securement strips comprising elastic bands, wherein each of the elastic bands have a plurality of stretched elastic members with opposed sides and being sandwiched between a pair of flexible sheets while in the stretched condition.

2. The support of claim 1 wherein the securing means comprises buttons.

3. The support of claim 1 wherein said elastic belt is endless.

4. The support of claim 1 wherein said securement strips are elastic.

5. The support of claim 1 wherein at least one of the sheets comprises a woven material.

6. The support of claim 1 wherein at least one of the sheets comprises a nonwoven material.

7. The support of claim 1 wherein at least one of the sheets comprises a plastic film.

* * * * *